US008926582B2

(12) United States Patent
Wahl et al.

(10) Patent No.: US 8,926,582 B2
(45) Date of Patent: Jan. 6, 2015

(54) SEALING CAP FOR A BODY FLUID CONTAINER AND A BLOOD COLLECTION DEVICE

(75) Inventors: Hans-Peter Wahl, Schopfheim (DE); Rolf Schneebeli, Mettmenstetten (CH); Renato Belz, Emmenbrucke (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1063 days.

(21) Appl. No.: 12/617,070

(22) Filed: Nov. 12, 2009

(65) Prior Publication Data

US 2010/0113976 A1 May 6, 2010

Related U.S. Application Data

(63) Continuation of application No. PCT/EP2008/004080, filed on May 21, 2008.

(30) Foreign Application Priority Data

May 25, 2007 (EP) .................................... 07010483

(51) Int. Cl.
*A61M 5/32* (2006.01)
*A61B 5/15* (2006.01)
*B01L 3/00* (2006.01)

(52) U.S. Cl.
CPC ....... *B01L 3/50825* (2013.01); *B01L 2300/044* (2013.01); *B01L 2300/0672* (2013.01)
USPC .................. 604/411; 141/1; 141/2; 141/329; 215/235; 215/238; 215/247; 600/576; 600/577; 604/533; 604/537

(58) Field of Classification Search
USPC ................. 141/1, 2, 329; 215/235, 238, 247; 600/576, 577; 604/411, 533, 537
See application file for complete search history.

(56) References Cited

U.S. PATENT DOCUMENTS 3,659,587 A * 5/1972 Baldwin ...................... 600/577
3,729,031 A * 4/1973 Baldwin .......................... 141/2

(Continued)

FOREIGN PATENT DOCUMENTS

FR 2560049 8/1985
FR 2794435 A1 6/1999

(Continued)

OTHER PUBLICATIONS

International Search Report for Appl. No. PCT/EP2008/004080, now publication No. WO 2008/145294A1, dated Dec. 4, 2008, date of search report Sep. 16, 2008, (4 pages).

*Primary Examiner* — Sean Dougherty
(74) *Attorney, Agent, or Firm* — Dinsmore & Shohl LLP

(57) ABSTRACT

A sealing cap for a body fluid container, and a body fluid collection device and system are disclosed. The sealing cap includes an inner cap placeable on an opening in the body fluid container forming a mouth, the inner cap has a shielding member which seals the mouth of the body fluid container, an outer cap resting on the inner cap, the outer cap being movable relative to the inner cap, and a channel member, wherein by a rotational movement the outer cap is movable between an first position in which the channel member is located separated from the shielding member and a second position in which the channel member extends through the shielding member, thereby establishing an open state of the shielding member, and wherein the shielding member returns to a closed state when the outer cap is moved back from the second position to the first position.

12 Claims, 4 Drawing Sheets

(56) References Cited

U.S. PATENT DOCUMENTS

| | | | | | |
|---|---|---|---|---|---|
| 4,300,404 | A * | 11/1981 | Mehl et al. | 73/863.52 |
| 4,722,449 | A | 2/1988 | Dubach | |
| 4,994,029 | A * | 2/1991 | Rohrbough | 604/88 |
| 5,024,256 | A | 6/1991 | Vadher | |
| 5,163,583 | A | 11/1992 | Whitworth | |
| 5,188,628 | A * | 2/1993 | Rani et al. | 604/405 |
| 5,425,920 | A | 6/1995 | Conti et al. | |
| 5,527,513 | A * | 6/1996 | Burns | 422/549 |
| 5,536,262 | A * | 7/1996 | Velasquez | 604/533 |
| 5,685,866 | A * | 11/1997 | Lopez | 604/249 |
| 5,688,254 | A * | 11/1997 | Lopez et al. | 604/535 |
| 5,817,082 | A * | 10/1998 | Niedospial et al. | 604/414 |
| 5,826,713 | A * | 10/1998 | Sunago et al. | 206/222 |
| 5,895,383 | A * | 4/1999 | Niedospial, Jr. | 604/403 |
| 5,954,104 | A * | 9/1999 | Daubert et al. | 141/329 |
| 5,954,233 | A * | 9/1999 | Kawashima et al. | 222/83 |
| 5,971,181 | A * | 10/1999 | Niedospial et al. | 215/247 |
| 6,024,235 | A * | 2/2000 | Schwab | 215/247 |
| 6,030,582 | A * | 2/2000 | Levy | 422/570 |
| 6,054,099 | A * | 4/2000 | Levy | 422/547 |
| 6,120,490 | A * | 9/2000 | Neftel | 604/411 |
| 6,139,534 | A * | 10/2000 | Niedospial et al. | 604/411 |
| 6,161,712 | A | 12/2000 | Savitz | |
| 6,209,738 | B1 * | 4/2001 | Jansen et al. | 215/247 |
| 6,258,078 | B1 * | 7/2001 | Thilly | 604/411 |
| 6,305,563 | B1 * | 10/2001 | Elliott | 215/235 |
| 6,325,782 | B1 * | 12/2001 | Lopez | 604/249 |
| 6,361,744 | B1 * | 3/2002 | Levy | 422/570 |
| 6,378,714 | B1 * | 4/2002 | Jansen et al. | 215/249 |
| 6,382,441 | B1 | 5/2002 | Carano | |
| 6,382,442 | B1 * | 5/2002 | Thibault et al. | 215/249 |
| 6,544,246 | B1 * | 4/2003 | Niedospial, Jr. | 604/411 |
| 6,571,837 | B2 * | 6/2003 | Jansen et al. | 141/329 |
| 6,716,396 | B1 * | 4/2004 | Anderson et al. | 422/501 |
| 6,723,289 | B2 * | 4/2004 | Iheme et al. | 422/501 |
| 6,733,465 | B1 * | 5/2004 | Smutney et al. | 600/576 |
| 6,752,965 | B2 * | 6/2004 | Levy | 422/570 |
| 6,806,094 | B2 * | 10/2004 | Anderson et al. | 436/180 |
| 6,832,994 | B2 * | 12/2004 | Niedospial et al. | 604/411 |
| 6,902,207 | B2 * | 6/2005 | Lickliter | 285/331 |
| 6,997,917 | B2 * | 2/2006 | Niedospial et al. | 604/411 |
| 7,276,383 | B2 * | 10/2007 | Iheme et al. | 436/180 |
| 7,309,469 | B2 * | 12/2007 | Anderson et al. | 422/550 |
| 7,387,216 | B1 * | 6/2008 | Smith | 220/254.3 |
| 7,435,389 | B2 * | 10/2008 | Anderson et al. | 422/501 |
| 7,645,274 | B2 * | 1/2010 | Whitley | 604/537 |
| 7,648,680 | B2 * | 1/2010 | Anderson et al. | 422/501 |
| 7,678,333 | B2 * | 3/2010 | Reynolds et al. | 422/554 |
| 7,748,379 | B2 * | 7/2010 | Rasor et al. | 128/200.24 |
| 7,803,124 | B2 * | 9/2010 | Eberhart et al. | 600/585 |
| 7,824,921 | B1 * | 11/2010 | Levy | 436/180 |
| 8,221,381 | B2 * | 7/2012 | Muir et al. | 604/415 |
| 8,267,127 | B2 * | 9/2012 | Kriheli | 141/1 |
| 8,631,953 | B2 * | 1/2014 | Pavlovic et al. | 215/249 |
| 2001/0003996 | A1 | 6/2001 | Jansen | |
| 2001/0041336 | A1 * | 11/2001 | Anderson et al. | 435/6 |
| 2002/0079285 | A1 * | 6/2002 | Jansen et al. | 215/249 |
| 2002/0131902 | A1 * | 9/2002 | Levy | 422/99 |
| 2003/0052074 | A1 * | 3/2003 | Chang et al. | 215/247 |
| 2003/0205901 | A1 * | 11/2003 | Lickliter | 285/921 |
| 2003/0207463 | A1 * | 11/2003 | Iheme et al. | 436/180 |
| 2004/0112457 | A1 * | 6/2004 | Norton et al. | 141/26 |
| 2004/0129343 | A1 * | 7/2004 | Jansen et al. | 141/329 |
| 2004/0151634 | A1 * | 8/2004 | Anderson et al. | 422/99 |
| 2005/0059161 | A1 * | 3/2005 | Anderson et al. | 436/174 |
| 2005/0124964 | A1 * | 6/2005 | Niedospial et al. | 604/411 |
| 2006/0030832 | A1 * | 2/2006 | Niedospial et al. | 604/411 |
| 2006/0142735 | A1 * | 6/2006 | Whitley | 604/537 |
| 2006/0208210 | A1 * | 9/2006 | Raybuck | 251/149.1 |
| 2007/0021721 | A1 * | 1/2007 | Lopez | 604/249 |
| 2007/0032775 | A1 * | 2/2007 | Niedospial et al. | 604/415 |
| 2007/0181522 | A1 * | 8/2007 | Davidson | 215/228 |
| 2008/0047371 | A1 * | 2/2008 | Anderson et al. | 73/863.21 |
| 2008/0073348 | A1 * | 3/2008 | Pritikin et al. | 220/278 |
| 2008/0223815 | A1 * | 9/2008 | Konrad | 215/329 |
| 2008/0290060 | A1 * | 11/2008 | Ammann | 215/228 |
| 2009/0216213 | A1 * | 8/2009 | Muir et al. | 604/414 |
| 2014/0242685 | A1 * | 8/2014 | Knoppke et al. | 435/289.1 |

FOREIGN PATENT DOCUMENTS

| | | |
|---|---|---|
| JP | 3050685 | 5/1998 |
| JP | 2005324832 A | 11/2005 |
| WO | 9837855 | 9/1998 |
| WO | 2006/132041 A1 | 12/2006 |

* cited by examiner

SEALING CAP FOR A BODY FLUID CONTAINER AND A BLOOD COLLECTION DEVICE

CROSS REFERENCE TO RELATED APPLICATIONS

The present application is filed under 35 U.S.C. §111 (a) as a continuation of copending International Application No. PCT/EP2008/004080, with an international filing date of May 21, 2008,and claims priority under 35 U.S.C. §119 to European Patent Application No. 07010483.1, filed May 25, 2007,now EP Patent No. 2148823.

TECHNICAL FIELD

Embodiments of the invention relate to a sealing cap for a body fluid container and a blood collection device for collecting a blood sample.

BACKGROUND

Containers for body fluid collection and storage are known in many different versions. Among such containers are blood collection devices provided as blood collection tubes. State of the art blood collection tubes have commonly been provided with a thick rubber stopper also referred to as a cap which can be pierced with sharp needles using much force. The collection tubes are used as primary containers in laboratory analyzers. Today, the "usual" practice in laboratories is for the blood collection tubes to be opened before they are placed in an analysis machine in that the cap is removed either manually or using a decapper.

Body fluid containers with caps have been found whereby the rubber stopper is pre-pierced with a plastic device creating an opening through which pipetting is possible. Examples include devices disclosed in U.S. Pat. Nos. 5,240,679 and 5,081,872. Other devices and machines are known from U.S. Pat. No. 4,974,457 and WO 90/11752. Both processes mentioned above use disposable plastic parts. Furthermore, there are methods which press a washable hollow needle through the rubber cap which one may then pipette through (see U.S. Pat. No. 5,270,211). All of the systems were not able to establish themselves and have disappeared from the market once more.

The disadvantages of the prior art devices are that both of the above methods require a special device and particular equipment in order to provide the considerable force necessary to penetrate the cap. This can regularly lead to breakages in the tube container and the resulting contamination of the device, which is the exact opposite of the desired aim, namely a more or less contamination-free pipetting from "closed" tube containers. The other methods had the disadvantage of the hollow needle which must be cleaned or in cases of direct pipetting through the vacutainer's stopper, the forces necessary are particularly high and therefore it is not possible to pipette small volumes accurately due to the negative pressure which was thereby created in the tube container. A further disadvantage of existing solutions is that tube containers which do not have the device mentioned above are normally opened (decapped) before they are placed in the analysis equipment and have to receive a new closure (be recapped) prior to storage in a refrigerator. This has to be done for each subsequent analysis.

U.S. Pat. No. 6,116,445 discloses a sealing cap for the mouth of a container which facilitates both the sealing of new bottles containing unused contents, and the re-sealing of those bottles already in use so as to preserve their contents. The sealing cap includes an inner cap and an outer cap. The inner cap includes a shielding plate which is fixed on the mouth of a container, and an annular strip which is provided at the lower end of the outer circumferential wall of the inner cap. The outer cap, which is fixed on the inner cap, includes a top lid, and a main cap with a guide tube having a lower-end sharp edge located opposite the shielding plate. By removing the annular strip from the inner cap and pressing down the outer cap, the lower end of the outer cap engages the outer circumference of the mouth of the container, and at the same time, the lower-end sharp edge of the guide tube pierces the shielding plate. The user then opens the top lid of the outer cap to access the contents of the container.

From U.S. Pat. No. 6,024,234 a cap member having an annular wall and a top wall disposed within and connected to the annular wall is known. An arcuate pierce-plow member is disposed on an upper surface of the top wall at a position spaced from the annular wall. The pierce-plow member includes a piercing member disposed adjacent to the substantially flat portion of the plow base member. In an inverted, operative position relative to the container having a pierceable membrane which fluidly seals the mouth, the cap member can be used to pierce the pierceable membrane by rotating the cap member.

SUMMARY

Embodiments of the invention provide an improved sealing cap for a body fluid container, and a body fluid collection device, which facilitates the handling of a body fluid sample for the user, especially a blood sample.

According to an embodiment of the invention a sealing cap for a body fluid container, is provided, the sealing cap comprising: an inner cap to be placed on an opening in the body fluid container forming a mouth, the inner cap comprising a shielding member to seal the mouth of the container, an outer cap resting on the inner cap, the outer cap being movable relative to the inner cap, a channel member, wherein by a rotational movement the outer cap is movable between a first position, in which the channel member is located separated from the shielding member, and a second position, in which the channel member is extending through the shielding member, thereby establishing an open state of the shielding member, and wherein the shielding member returns to a closed state when the outer cap is moved back from the second position to the first position.

According to another embodiment of the invention, a body fluid collection device for collecting a body fluid sample, e.g. a blood sample, is provided, the device comprising a body fluid container and a sealing cap according to the above described embodiment placed on an opening in the body fluid container forming a mouth.

According to still another embodiment of the invention, a body fluid collection system for collecting a body fluid sample is provided, the body fluid collection system comprising a body fluid container and a sealing cap according to the above described embodiment placed on an opening in the body fluid container forming a mouth and a pipetting device.

BRIEF DESCRIPTION OF THE DRAWINGS

In the following, the invention will be described in further detail, by way of example, with reference to different embodiments. In the figures show.

In the FIG. 1 to 4, the same features are referred to by identical reference numerals.

DETAILED DESCRIPTION

Figure 1:
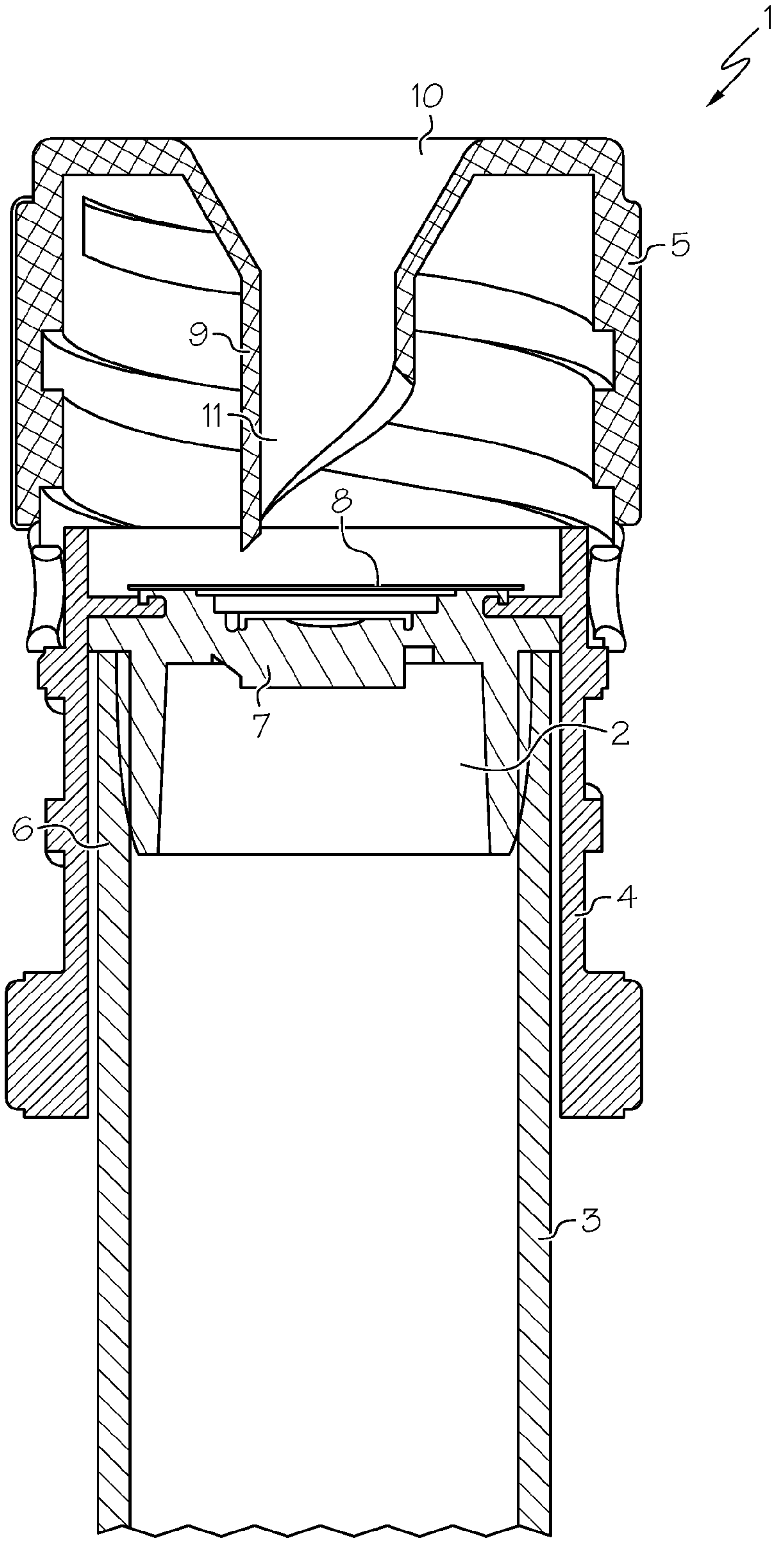
FIG. 1 an arrangement with a sealing cap placed on an opening in a body fluid container forming a mouth of the body fluid container, wherein an outer cap is in a starting position, FIG. 2 the arrangement with the sealing cap placed on the opening in the body fluid container, wherein the outer cap is still in the starting position, but blood sample has been aspired already, FIG. 3 the arrangement with the sealing cap placed on the opening in the body fluid container, wherein the outer cap is in a lower position, and FIG. 4 the arrangement with the sealing cap placed on the opening in the body fluid container, wherein the outer cap is in an upper position.

According to an embodiment of the invention a sealing cap for a body fluid container, is provided, the sealing cap comprising: an inner cap to be placed on an opening in the body fluid container forming a mouth, the inner cap comprising a shielding member to seal the mouth of the container, an outer cap resting on the inner cap, the outer cap being movable relative to the inner cap, a channel member, wherein by a rotational movement the outer cap is movable between a first position, in which the channel member is located separated from the shielding member, and a second position, in which the channel member is extending through the shielding member, thereby establishing an open state of the shielding member, and wherein the shielding member returns to a closed state when the outer cap is moved back from the second position to the first position. The sealing cap, for example, may be used for sealing a blood collection tube.

An embodiment of the invention comprises the idea of movably mounting the outer cap onto the inner cap in such a way that the outer cap is located in a first position, which could also be referred to as the upper position, in which the channel member forming part of the outer cap is located separated from the shielding member, specifically above this. When the sealing cap is located on top of the container, this constitutes a closed interior of the container. The outer cap can be moved, by means of a downwards rotational movement, into the second position in which the channel member extends through the shielding member, thus creating an access to the interior of the container through which a body fluid can either flow directly or be extracted using suitable equipment, for example a pipette. The tip of the latter can be inserted via the body fluid channel in the channel member. Through a reverse rotational movement, the outer cap can be moved back upwards to remove the channel member from the area of the shielding member. The outer cap is guided between the first and second positions in its rotational movement with the help of guiding means. In this way, the use of the cap is made easier as through the help of the guiding means, the upward and downward movement of the outer cap is clearly determined. It is not left to the user, as to how much pressure he uses to open the outer cap. Rather, the guiding means define the movement of the outer cap relative to the inner cap in a particular way. The probability of damaging elements of the sealing cap is thus reduced.

In order to form the closed state, one embodiment sees a section of the shielding member, previously pushed to one side by the channel member, return to its starting position thus closing the interior of the container once more, in respect to the environment. Even though such a re-sealings usually less tight than the original seal, the container is closed in this way after body fluid has been collected in or extracted from the container and as such a further storage of the body fluid in the container is made possible.

The sealing cap or the body fluid collection device can be provided as sterile packaged articles, in particular also as disposable products.

In a preferred embodiment, the guiding means are configured to guide the outer cap on a helical path in the rotational movement between the first and second position. The configuration of a helical path supports an even and gradual raising and lowering of the outer cap relative to the inner cap, whereby the outer cap slides smoothly into the second position.

In a further embodiment still, the channel member is provided with a bottom-end piercing edge, configured to pierce the shielding member when the outer cap is moved from the first position to the second position for the first time by the rotational movement. With the help of the bottom-end piercing edge, the shielding member is pierced and cut in such a way that a section of the shielding member can be pushed to one side by the channel member as the channel member passes through the shielding member. The bottom-end piercing edge can be configured in an embodiment such that the cutting or piercing of the shielding member through the downward rotational movement of the outer cap takes place gradually.

According to a preferred embodiment, the bottom-end piercing edge is configured to pierce the shielding member along an annular piercing line. Such annular piercing line, in a preferred embodiment, may be an open circle line.

In order to form the closed state, one embodiment sees a section of the shielding member, previously pushed to one side by the channel member, return to its starting position thus closing the interior of the container once more, in respect to the environment. Even though such a re-sealing is usually less tight than the original seal, the container is closed in this way after body fluid has been collected in or extracted from the container and as such a further storage of the body fluid in the container is made possible.

In an embodiment, restriction means are provided, the restriction means being configured to hold the outer cap in a used first position different from an unused first position when the outer cap is moved from the second position into the first position. In one embodiment, the restriction means are provided on facing surfaces of the outer cap and the inner cap. For example, on the outer cap a projection is located which interacts with a recess on the inner cap. The projection slides over the recess in the downwards rotational movement of the outer cap, but jumps into the recess in the upwards rotational movement of the outer cap, thereby providing a locked connection between the inner and outer cap. Also other engagement mechanism may be provided permitting the downwards rotational movement of the outer cap and securing the outer cap in the used first position.

According to a further embodiment, position label means are provided, configured to indicate at least one of the unused first position and the used first position of the outer cap. In this way, there is an external indication as to whether the sealing cap is in its original state or a used state. The latter is characterized by the fact that the cap has already been moved into the second position at least once, and thus an opening exists to the interior of the container for the collection or extraction of body fluid. It is thus, in practice, immediately evident to the user as to whether the container has been used or not. A colored marking as a position label means is preferred.

In a further embodiment still, wherein the shielding member comprise a pierceable sealing membrane, the sealing membrane is in one embodiment made of aluminium foil. This has a coating made of one of polypropylene and polyethylene which is used to further seal the aluminium membrane, for example with suitable conditions in respect of temperature and pressure. A similar sealing is also possible using a sealing membrane made of other materials. The pierceable sealing membrane is configured to avoid penetration of a body fluid including gas. Therefore, in a container sealed by the sealing cap a vacuum can be kept until the pierceable sealing membrane is pierced, for example until the container is filled with a blood sample from a patient in a phlebotomy. In order to fill the container with a blood sample in the scope of a blood test, a cannula is inserted through the sealing membrane and further through the shielding member.

According to a preferred embodiment, the outer cap is provided as a molded member made of a plastic material. In another preferred embodiment, the inner cap is made of an elastic material such as a thermoplastic elastomer or rubber.

In another preferred embodiment, guiding means are provided, configured to guide the outer cap relative to the inner cap in the rotational movement between the first and second position.

In a preferred embodiment, the guiding means comprise threads configured to provide a threaded connection between the outer cap and the inner cap.

In still a further embodiment, the channel member is provided with a passage for a pipetting device. In a preferred embodiment, the passage is provided with a diameter in the range from about 3 mm to about 11 mm.

In a preferred embodiment, the inner cap is provided as a stopper member, the stopper member comprising an inner circumferential wall and an outer circumferential wall.

According to another embodiment of the invention, a body fluid collection device for collecting a body fluid sample, e.g. a blood sample, is provided, the device comprising a body fluid container and a sealing cap according to any of the above described embodiments placed on an opening in the body fluid container forming a mouth.

According to still another embodiment of the invention, a body fluid collection system for collecting a body fluid sample is provided, the body fluid collection system comprising a body fluid container and a sealing cap according to any of the above described embodiments placed on an opening in the body fluid container forming a mouth and a pipetting device. The pipetting device, for example, is provided as a pipetting needle.

FIGS. 1 to 4 show a sealing cap 1, with which a mouth 2 of a container 3 is closed. The container 3 is, for example, a tube for the collection of an extracted bodily fluid, in particular a blood sample, but can be used also for storage of other body fluids. The sealing cap 1 comprises an inner cap 4 and an outer cap 5, which rests on the inner cap 4. The inner cap 4 is mounted on a wall 6 of the container 3. The mouth 2 of the container 3 is sealed body fluid-tight with the help of a shielding member 7 which forms part of the inner cap 4. Such a starting position is shown in FIG. 1. The shielding member 7 is also covered with a sealing membrane 8 which supports the body fluid-tight seal of the container 3, especially a gas-tight seal. The preferred form of the sealing membrane 8 is a coated foil, such as aluminum foil, which is sealed onto the shielding member 7.

In the starting position of the outer cap 5, as per FIG. 1, a channel member or piercing member 9 is located above the shielding member 7 and the sealing membrane 8. With the help of the channel member 9, an opening 10 is formed in the outer cap 5 through which a channel or passage 11 runs which is configured to receive a pipetting device (not shown).

Figure 2:
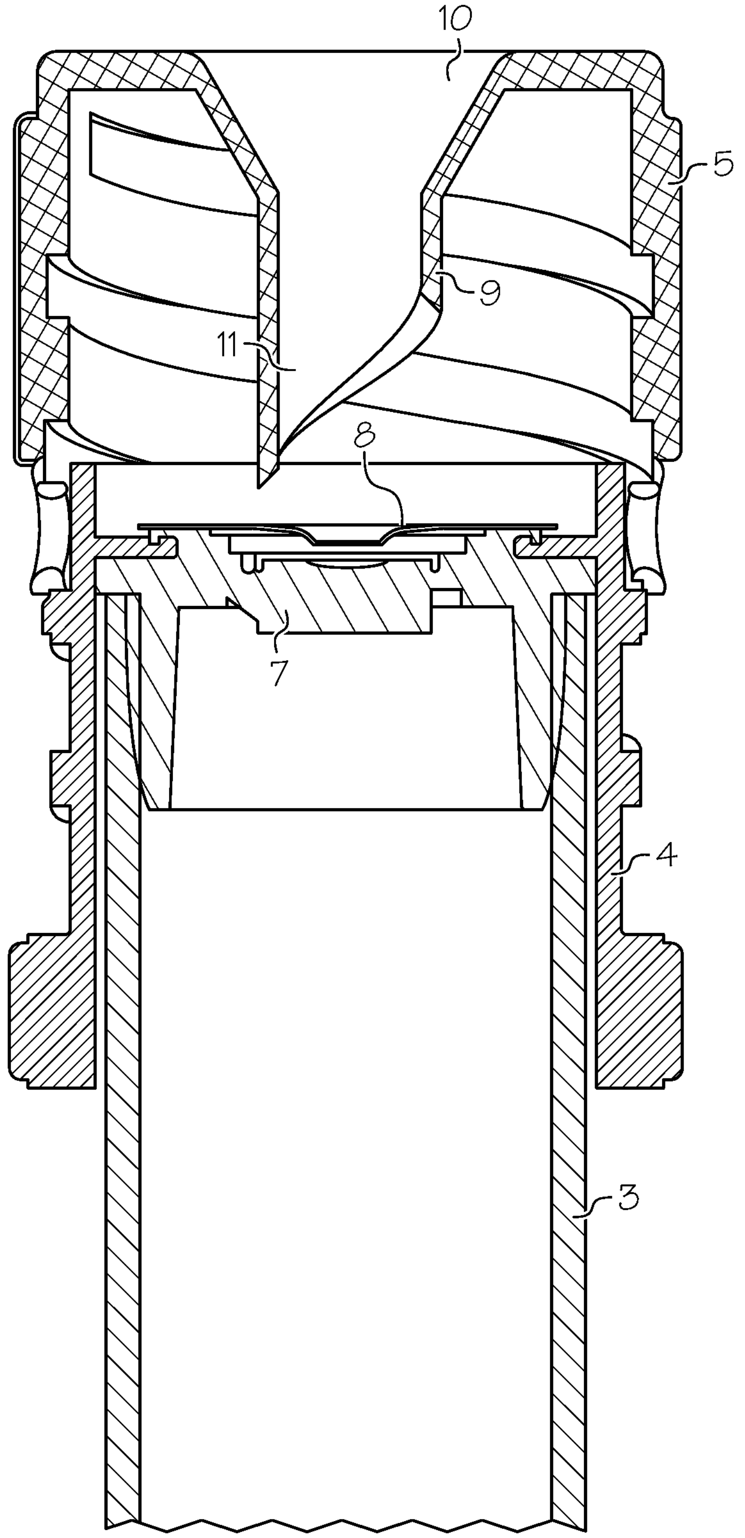

In order to fill the container 3 with a blood sample in the scope of a blood test, a cannula (not shown) is inserted through the opening 10 into the channel 11 and then further through the sealing membrane 8 and the shielding member 7. The outer cap 5 hereby preferably remains in the position shown in FIG. 1. In this way the blood sample can be collected in the container 3 in the course of a blood test. FIG. 2 shows the situation after blood sample has been collected using the method described above as the sealing membrane is now, in contrast to FIG. 1, pushed downwards at least in the centre due to the prior piercing or cutting. The temporary opening in the shielding member 7, formed through the piercing with the cannula is automatically re-sealed due to the material of the shielding member 7, for example rubber or a thermo-plastic elastomer.

Figure 3:
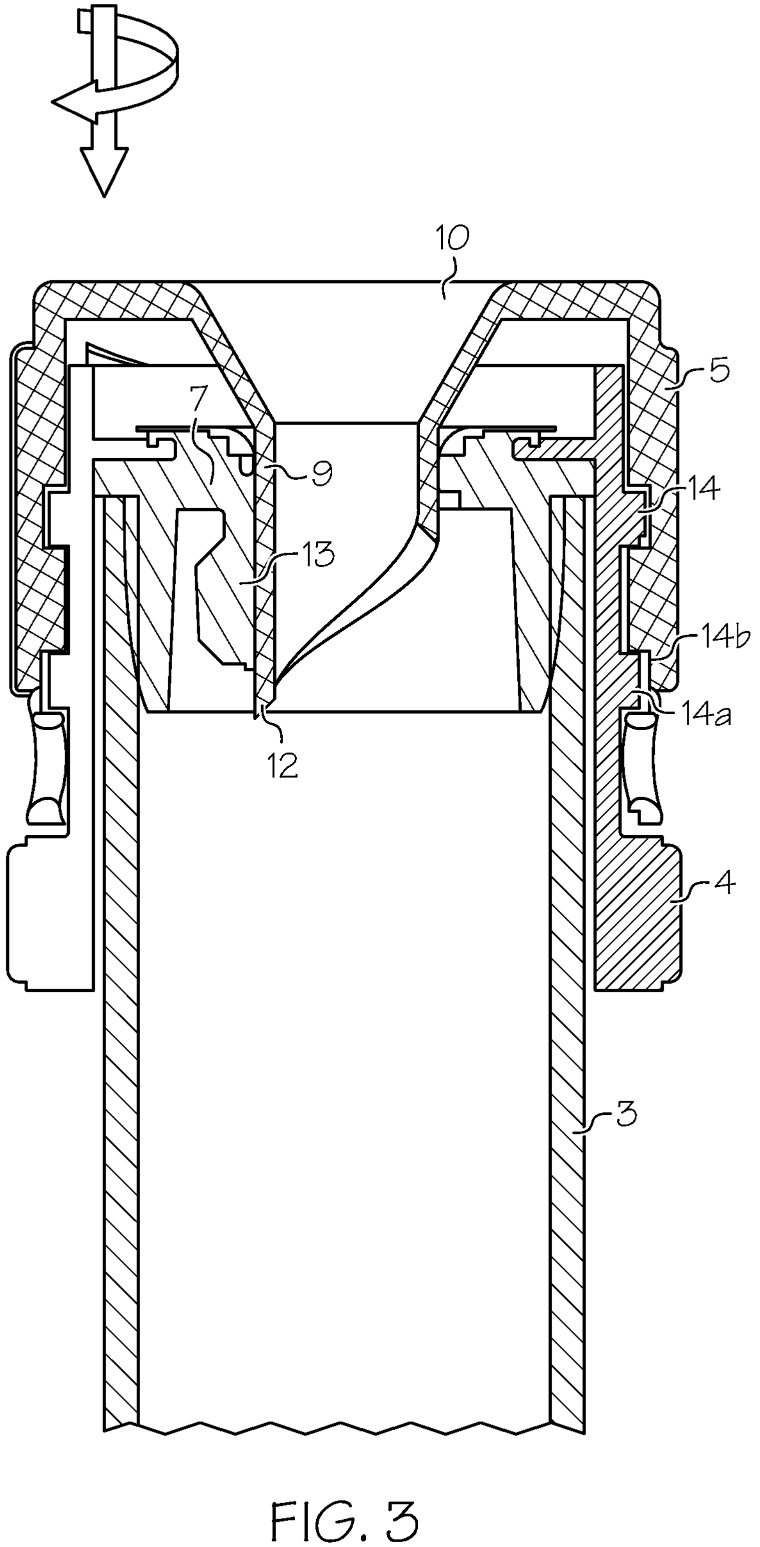

FIG. 3 shows the outer cap 5 in a second position which is characterized by the fact that the channel member 9 extends through the shielding member 7. In this way, access is gained to the interior of the container 3 through the channel 11 in the channel member 9, for example using a syringe or the tip of a pipette in order to remove part of the blood sample. The moving of the outer cap 5 into the second position as shown in FIG. 3 is achieved by rotating the outer cap 5 relative to the inner cap 4. This rotational movement of the outer cap 5 leads to a guided downwards movement of the outer cap 5 whereby a piercing or cutting edge 12 pierces or cuts through the shielding member 7 which subsequently leads to a section 13 of the shielding member 7 being pushed to one side by the channel member 9 as shown in FIG. 3. The piercing or cutting edge 12 cuts the shielding member 7 gradually, along an open annular piercing line, without completely separating the section 13.

The movement of the outer cap 5 downwards in the course of the rotational movement is guided by threads 14, the interlocking elements 14*a* and 14*b* provided on the inner and outer caps 4 and 5 respectively.

Figure 4:
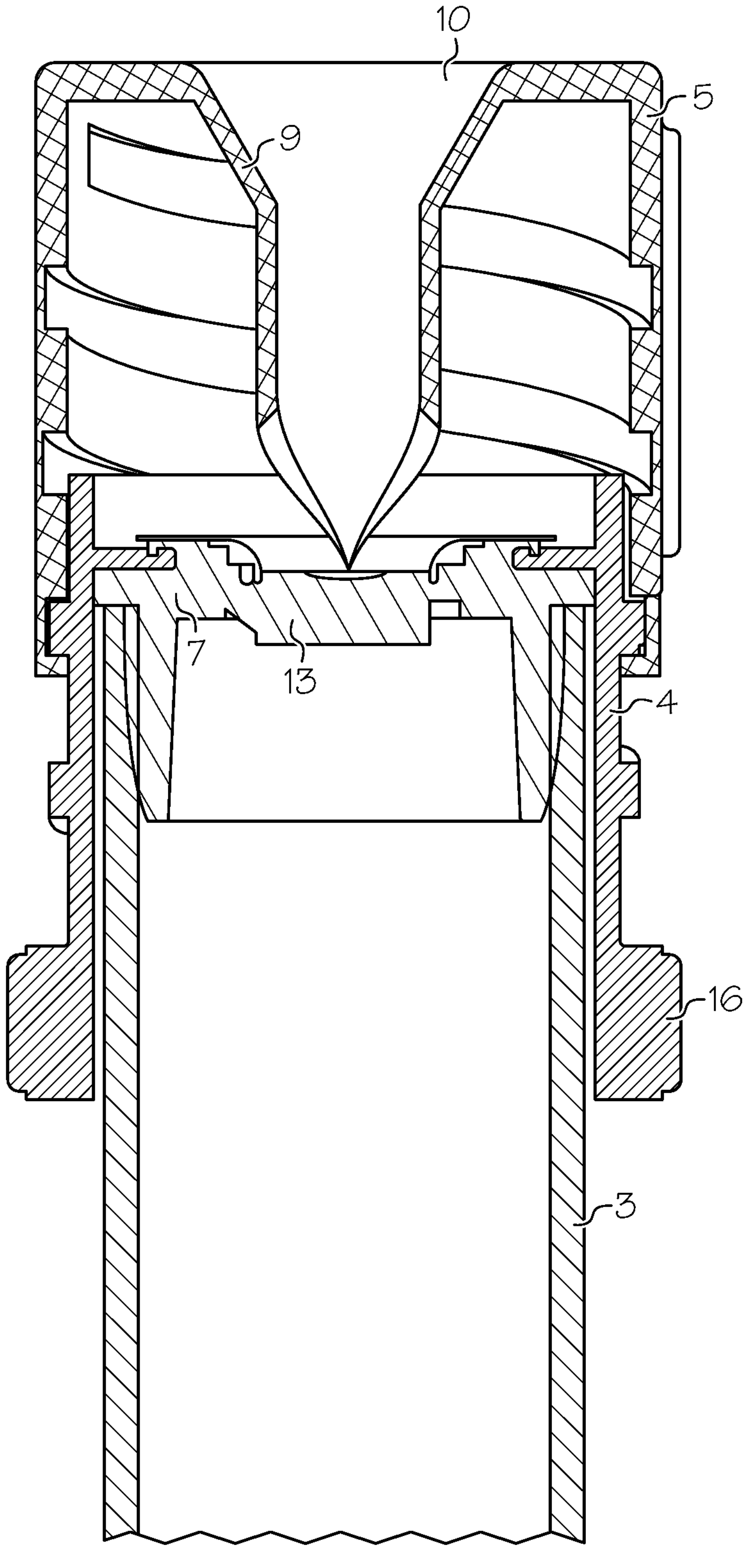

After a body fluid sample has been removed from the container 3 or body fluid has been collected in the container 3 the outer cap 5 can be moved back upwards again with a screw or rotational movement in the opposite direction, as shown in FIG. 4. The channel member 9 is located above and separated from the shielding member 7 once more. In fact, the outer cap 5 is not returned to the starting position shown in FIG. 1. This is prevented through the use of restriction means (not shown), preferably provided on the threads 14. Such restriction means which may be provided as a locking connection secure the outer cap 5 in the position shown in FIG. 4, but permit the rotational movement. Whether or not the outer cap 5 is in the starting position shown in FIG. 1 or in the position in FIG. 4 is helpfully indicated to the user through a suitable marking on the sealing cap 1. For example the outer cap 5 could have an opening which overlaps with a colored marking on the inner cap 4 whereby a different color is visible to the user through the opening depending on the position of the outer cap 5.

In FIG. 4, the section 13 of the shielding member 7, shown pushed to one side in FIG. 3, has returned to its starting position so that the shielding member 7 seal the container 3 once more. Any remaining blood, or other body fluid, can thus be stored further, for example in a refrigerator. The outer cap 5 can be moved into the position shown in FIG. 3 several times in order to remove or add body fluid samples. Each time the outer cap 5 is subsequently returned to the position in FIG. 4 through the rotational movement, the container 3 is re-closed with the help of the shielding member 7.

In its lower part, the inner cap 4 has thicker sections 16 which comprise a possible embodiment of grip elements which facilitate the attachment and removal of the sealing cap 1.

Although preferred embodiments of the invention have been described using specific terms, such description is for illustrative purposes only, and it is to be understood that changes and variations obvious to the skilled artisan are to be considered within the scope of the claims that follow and their equivalents.

What is claimed is:

1. A sealing cap for a body fluid container, the sealing cap comprising:

an inner cap placeable on an opening that forms a mouth in the body fluid container, the inner cap comprising a shielding member which seals the mouth of the body fluid container and a first interlocking element for forming a threaded connection;

an outer cap comprising a second interlocking element for forming the threaded connection, wherein the first interlocking element of the inner cap and the second interlocking element of the outer cap forms the threaded connection between the inner cap and the outer cap such that the outer cap is movable relative to the inner cap; and a channel member forming part of the outer cap, the channel member comprising a passage configured to receive a pipetting device, wherein:

while the threaded connection is formed between the inner cap and the outer cap, the outer cap slides by a rotational movement along the inner cap between a first position and a second position;

when the outer cap is in the first position, the channel member is located separated from the shielding member and a portion of the shielding member is at an initial sealing position, such that the shielding member is in a closed state;

when the outer cap is in the second position, the channel member extends through the shielding member and the portion of the shielding member is moved downwards and aside from the initial sealing position by the channel member, thereby establishing an open state of the shielding member; and when the outer cap is moved back from the second position to the first position, the shielding member returns to the initial sealing position to place the shielding member in the closed state.

2. The sealing cap according to claim 1, wherein the channel member is provided with a bottom-end piercing edge, configured to pierce the shielding member when the outer cap is moved from the first position to the second position for a first time by the rotational movement.

3. The sealing cap according to claim 2, wherein the bottom-end piercing edge is configured to pierce the shielding member along an annular piercing line.

4. The sealing cap according to claim 1, wherein restriction means are provided, the restriction means being configured to hold the outer cap in a used first position different from an unused first position when the outer cap is moved from the second position into the first position.

5. The sealing cap according to claim 4, wherein position label means are provided, configured to indicate at least one of the unused first position and the used first position of the outer cap.

6. The sealing cap according to claim 1, wherein the shielding member comprise a pierceable sealing membrane.

7. The sealing cap according to claim 1, wherein the outer cap is provided as a molded member made of a plastic material.

8. The sealing cap according to claim 1, wherein the first interlocking element and the second interlocking element are configured to guide the outer cap on a helical path in the rotational movement between the first and second position.

9. The sealing cap according to claim 1, wherein the inner cap is made of an elastic material such as a thermoplastic elastomer or rubber.

10. The sealing cap according to claim 1, wherein the inner cap is provided as a stopper member, the stopper member comprising an inner circumferential wall and an outer circumferential wall.

11. A body fluid collection device for collecting a body fluid sample, the device comprising:

a body fluid container; and a sealing cap according to claim 1 placed on an opening in the body fluid container forming a mouth.

12. A body fluid collection system for collecting a body fluid sample, the body fluid collection system comprising:

a body fluid container;

a sealing cap according to claim 1 placed on an opening in the body fluid container forming a mouth; and a pipetting device.

* * * * *